(12) United States Patent
Singh et al.

(10) Patent No.: US 8,404,853 B2
(45) Date of Patent: Mar. 26, 2013

(54) PROCESS FOR THE PREPARATION OF OPTICALLY PURE OR OPTICALLY ENRICHED ENANTIOMERS OF SULPHOXIDE COMPOUNDS

(75) Inventors: Girij Pal Singh, Pune (IN); Himanshu Madhav Godbole, Pune (IN); Narotham Maddireddy, Pune (IN); Suhas Ganpat Tambe, Pune (IN); Sagar Purushottam Nehate, Pune (IN); Harischandra Sambhaji Jadhav, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 693 days.

(21) Appl. No.: 12/307,399

(22) PCT Filed: Oct. 5, 2006

(86) PCT No.: PCT/IN2006/000398
§ 371 (c)(1),
(2), (4) Date: Mar. 3, 2010

(87) PCT Pub. No.: WO2008/004245
PCT Pub. Date: Jan. 10, 2008

(65) Prior Publication Data
US 2010/0160639 A1    Jun. 24, 2010

(30) Foreign Application Priority Data
Jul. 5, 2006 (IN) .............................. 676/KOL/2006

(51) Int. Cl.
C07D 401/12    (2006.01)
(52) U.S. Cl. ................................................. 546/273.7
(58) Field of Classification Search ................ 546/273.7
See application file for complete search history.

(56) References Cited

U.S. PATENT DOCUMENTS
5,948,789 A    9/1999    Larsson et al.

FOREIGN PATENT DOCUMENTS
| CN | 1223262 | 7/1999 |
|---|---|---|
| DE | 40 35 455 A1 | 5/1992 |
| WO | WO 94/27988 | 12/1994 |
| WO | WO 96/01707 | 1/1996 |
| WO | WO 96/17076 | 6/1996 |
| WO | WO 03/051867 A1 | 6/2003 |
| WO | WO 2004/002982 A2 | 1/2004 |
| WO | WO 2006/040635 A1 | 4/2006 |
| WO | WO 2006/094904 A1 | 9/2006 |
| WO | WO 2007/013743 A1 | 2/2007 |

OTHER PUBLICATIONS

Deng et al., "Resolution of omeprazole by inclusion complexation with a chiral hose BINOL," *Tetrahedron: Assymetry* Vol. 11 (2000). 1729-1732, XP002429856.

*Primary Examiner* — Patricia L Morris
(74) *Attorney, Agent, or Firm* — Merchant & Gould P.C.

(57) ABSTRACT

A process for preparation of optically pure or optically enriched enantiomers of sulphoxide compounds of formula (I), such as omeprazole and structurally related compounds, as well as their salts and hydrates. The said process comprises a) providing, a mixture of enantiomers of the sulphoxide compound of formula (I) as starting material, in an organic solvent; said enantiomers having R and S configurations at the sulfur atom of the sulphoxide group;

b) treating the mixture of enantiomers, in the organic solvent, with a chiral host;

c) separating the adduct formed by the enantiomer and the chiral host;

d) if desired, repeating the operation of step (b);

e) treating the adduct obtained in step (c) or (d) with metal base selected from Group I and Group II metal, thereby obtaining metal salt of one of the optical isomers of the sulphoxide compound in optically pure or optically enriched form;

f) optionally, converting the Group I metal salt of optically pure or optically enriched form the optical isomers of the sulphoxide compound obtained in step (e) to magnesium salt.

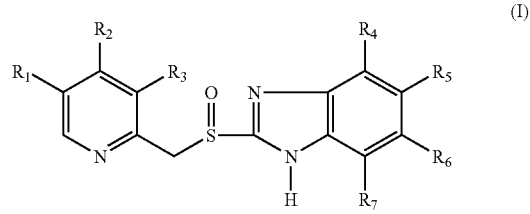

24 Claims, 5 Drawing Sheets

PROCESS FOR THE PREPARATION OF OPTICALLY PURE OR OPTICALLY ENRICHED ENANTIOMERS OF SULPHOXIDE COMPOUNDS

This application is a National Stage Application of PCT/IN20078/004245, filed Oct. 5, 2006, which claims benefit of Serial No. 676/KOL/2006, filed Jul. 5, 2006 in India and which application(s) are incorporated herein by reference. To the extent appropriate, a claim of priority is made to each of the above disclosed applications.

FIELD OF THE INVENTION

The present invention relates to a process for preparation of optically pure or optically enriched enantiomers of sulphoxide compounds, such as omeprazole and structurally related compounds, as well as their salts and hydrates.

BACKGROUND OF THE INVENTION

Substituted 2-(2-pyridinylmethylsulphinyl)-1H-benzimidazoles of formula (I) are useful

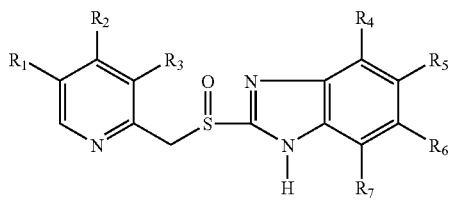

as inhibitors of gastric acid secretion.
wherein $R_1$, $R_2$ and $R_3$ are the same or different and selected from hydrogen, alkyl, alkylthio, alkoxy optionally substituted by fluorine, alkoxyalkoxy, dialkylamino, and halogen; $R_4$-$R_7$ are the same or different and selected from hydrogen, alkyl, alkoxy, halogen, halo-alkoxy, alkylcarbonyl, alkoxycarbonyl, and trifluoroalkyl.

For example, the compounds with generic names omeprazole, lansoprazole, rabeprazole, pantoprazole are used in the treatment of peptic ulcer. These compounds have a chiral center at the sulphur atom and thus exist as two optical isomers, i.e. enantiomers.

It has been well recognized in several pharmacologically active compounds that one of the enantiomer has superior biological property compared to the racemate and the other isomer.

For example, omeprazole (CAS Registry No. 73590-58-6), chemically known as 5-methoxy-2-{[(4-methoxy-3,5-dimethyl-2-pyridinyl)methyl]sulphinyl}-1H-benzimidazole, is a highly potent inhibitor of gastric acid secretion. It has a chiral center at the sulphur atom and exists as two enantiomers (S)-(−)-omeprazole and (R)-(+)-omeprazole. It has been shown that the (S)-enantiomer of omeprazole has better pharmacokinetic and metabolic properties compared to omeprazole. The (S)-enantiomer of omeprazole having generic name esomeprazole is marketed by Astra Zeneca in the form of magnesium salt under the brand name NEXIUM®. Therefore, there is a demand and need for an industrial scale process for manufacturing esomeprazole.

The methods of synthesis of racemic sulphoxide compounds of formula (I) are very successful for a large-scale industrial manufacture. However, the production of optically pure sulphoxide compounds of formula (I) is not easy.

The prior art methodologies for the preparation of single enantiomers of sulphoxides of formula (I) are based on enantioselective or chiral synthesis, optical resolution of the racemate, separation by converting the racemate to diastereomers, or by chromatography.

For example, some of the earliest prior art on enantioselective synthesis of the single enantiomers of sulphoxides of formula (I) described in Euro. J. Biochem. 166, (1987), 453, employed asymmetric sulphide oxidation process developed and reported by Kagan and co-workers in J. Am. Chem. Soc. 106 (1984), 8188. The process disclosed therein provides sulphoxide products in an enantiomeric excess of only about 30%, which upon several recrystallization steps yielded optically pure sulphoxide up to an e.e. of 95%. The oxidation was performed by using tert-butyl hydroperoxide as oxidizing agent in the presence of one equivalent of a chiral complex obtained from Ti(OiPr)$_4$/(+) or (−)-diethyl tartrate/water in the molar ratio of 1:2:1. A minimum of 0.5 equivalent of titanium reagent was found to be a must for obtaining very high enantioselectivity.

An improvement in the above oxidation process to obtain higher enantioselectivity was reported by Kagan and co-workers in Tetrahedron (1987), 43, 5135; wherein tert-butyl hydroperoxide was replaced by cumene hydroperoxide. In their further study reported in Synlett (1990), 643; Kagan and co-workers found that high enantioselectivity can be obtained if the temperature is maintained between −20° C. to −40° C., and methylene chloride is used as a solvent.

In contrary to Kagan's observation of requirement of low temperature and chlorinated solvent like methylene chloride for high enantioselectivity of the chiral oxidation, Larsson et al in U.S. Pat. No. 5,948,789 (equivalent to PCT publication WO 96/02535) have described an enantioselective process for the synthesis of the single enantiomers of compound of formula (I) by the chiral oxidation of the pro-chiral sulphide of formula (Ia) utilizing a chiral titanium (IV) isopropoxide complex in solvent systems such as toluene, ethyl acetate at 20-40° C., and most importantly a base like amine such as triethyl amine or diisopropyl amine.

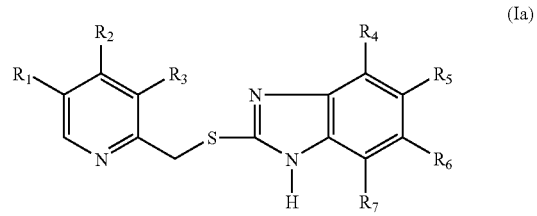

Although the formation of % e.e. of the desired isomer is satisfactory, the method suffers from the disadvantage (a) of low chemical conversion; (b) formation of undesired sulphide and sulfone impurities in substantial amounts, necessitating further purification by one or more tedious crystallization.

It is obvious from the above that such conversions which result in low chemical conversion and require costly metal complex and protracted purification, surely, is not desirable process for making a product such as optically active prazole in an industrial scale.

WO 96/17076 teaches a method of enantioselective biooxidation of the sulphide compound (Ia), which is effected by the action of Penicillium frequentans, Brevibacterium paraffinolyticum or Mycobacterium sp.

WO 96/1707 teaches the bioreduction of the racemic omeprazole to an enantiomer or enantiomerically enriched sulphide of formula (Ia), which is effected by the action of *Proteus vulgaris, Proteus mirabilis, Escherichia coli, Rhodobacter capsulatus* or a DMSO reductase isolated from *R. capsulatus*.

The separation of enantiomers of omeprazole in analytical scale is described in Marie et al.; *J. Chromatography*, 532, (1990), 305-19. WO 03/051867 describes a method for preparation of an enantiomerically pure or optically enriched enantiomer of either omeprazole, pantoprazole, lansoprazole, or raberpazole from a mixture containing the same using means for simulated moving bed chromatography with a chiral stationary phase such as amylose tris(S)-methylbenzycarbanmate. However, chromatographic methods are not suitable for large-scale manufacture of these prazoles.

The optical resolution methods taught in the art for separating the enantiomers of certain 2-(2-pyridinylmethylsulphinyl)-1H-benzimidazoles of formula (I) utilizes the diastereomer method, the crystallization method or the enzyme method.

The resolution process disclosed in DE 4035455 and WO 94/27988 involve converting the racemate 2-(2-pyridinylmethylsulphinyl)-1H-benzimidazoles to a diastereomeric mixture using a chiral acyl group, such as mandeloyl, and the diastereomers are separated and the separated diastereomer is converted to the optically pure sulphoxide by hydrolysis.

The method suffers from the following disadvantages,
(i) the resolution process involves additional steps of separation of diastereomeric mixture, and hydrolysis of the N-substituent in separated diastereomer,
(ii) the conversion of the racemate to diastereomeric acyl derivative is low yielding (~40%),
(iii) the diastereomer from the unwanted (R)-enantiomer is separated and discarded, WO 2004/002982 teaches a method for preparation of optically pure or optically enriched isomers of omeprazole by reacting the mixture of optical isomers with a chelating agent (D)-diethyl tartrate and transition metal complex titanium (IV) isopropoxide to form a titanium metal complex in an organic solvent such as acetone in presence of a base such as triethyl amine, which is then converted to salt of L-mandelic acid. The mandelic acid salt of the titanium complex of optical isomer derived from (S)-enantiomer of omeprazole gets precipitated, which is separated and purified to obtain chiral purity of about 99.8%.

Optically active 1,1'-bi-2-naphthol (BINOL) and its derivatives are useful as chiral ligands in catalysts for asymmetric reactions to hosts for molecular recognition and enantiomer separation, and often intermediates for the synthesis of chiral molecules.

BINOL is known to form crystalline complexes with a variety of organic molecules through hydrogen bonding. The (S) and/or (R) BINOL was found to be useful as a chiral host for enantioselective complexation. The application of BINOL in resolution of omeprazole is disclosed Deng et al in CN 1223262.

The Chinese patent application CN 1223262 (Deng et al) teaches the utility of chiral host compounds such as dinaphthalenephenols (BINOL), diphenanthrenols or tartaric acid derivatives in the resolution of prazoles. The method consists of formation of 1:1 solid complex between the chiral host and one of the enantiomer of the prazole, the guest molecule. The other enantiomer remains in the solution. The racemic prazole is treated with the chiral host in a mixture of solvent comprising of aromatic hydrocarbon solvents such as benzene, alkyl substituted benzene or acetonitrile and, hexane. The solid complex is separated from the solution, and dissolved again in a fresh solvent system by heating to 60-130° C. and then keeping at −20-10° C. for 6-36 hrs to obtain higher e.e. value for the solid complex. The process is repeated many times to obtain high e.e. values for the solid complex. The host and the guest in the solid complex are separated by column chromatography. The final separated single enantiomer of the prazole is then recrystallized from a mixture of methylene chloride or chloroform and, ether.

In a later publication in *Tetrahedron Asymmetry* 11 (2000), 1729-1732 the inventors of the above mentioned Chinese patent application reported the resolution of omeprazole using (S)-BINOL. An inclusion complex of (S)-BINOL and (S)-omeprazole was obtained as a grey-blue complex with 90.3% e.e. by mixing racemate omeprazole and (S)-(−)-BINOL in the mole ratio 1:1.5, in a solvent mixture of benzene:hexane (v/v=4:1) at 110° C. The inclusion complex obtained was further purified by recrystallization in benzene:hexane (v/v, 1:1) and separated on a silica gel column to yield (S)-(−)-omeprazole with 98.9% e.e. and 84.1% overall yield. The (S)-(−)-omeprazole so obtained was recrystallized in water to obtain as a white powder with 99.2% e.e.

In this publication, the authors have reported their observation of criticality of the benzene:hexane solvent ratio in obtaining the inclusion complex and the enantioselectivity. The authors reportedly have obtained the best enantioselectivity of 90.3% e.e. when the solvent ratio of benzene:hexane is 4:1 and the mole ratio of racemate omeprazole and (S)-(−)-BINOL is 1:1.5.

Further, by comparing the IR stretching frequencies observed for S=O bond in racemate omeprazole ($1018\,cm^{-1}$) and its inclusion complex with (S)-(−)-BINOL ($1028\,cm^{-1}$), the authors have concluded that the S=O bond which involved in a N—H . . . O=S hydrogen bond does not attribute the formation of hydrogen bonding in the inclusion complex, and the chiral recognition in the inclusion complex may occur via formation of hydrogen-bonded supramolecular chiron.

The method described in the above-mentioned Chinese patent application suffers in that,
(i) due to very low e.e. value for the solid complex obtained for the first time, the complexation process has to be repeated till the desired e.e. value is obtained,
(ii) to separate the host and the guest, one has to take recourse to tedious chromatographic methods,
(iii) overall the resolution involves several operations of complex formation, separation, purification by chromatography and recrystallization,
(iv) For the purpose of chromatography the amount silica and the solvent required is exorbitant
(v) with more operation steps, there is considerable material loss leading to lowering of the overall yield, which is not satisfactory for a commercial scale production,
(vi) the use of hexane with low flash point is not recommended for industrial processes,
(vii) volumes of the solvents to be handled having low flash point are quite large, necessitating special design of plant and machinery for safety,
(viii) benzene is carcinogenic and is listed as a class 1 solvent in ICH guideline.

Taking these considerations, the process disclosed in the CN 1223262 (Deng et al) does not give cost effective and eco-friendly method of manufacture.

It is evident from the above that there is a need for synthesizing optically pure sulphoxide compounds of formula (I), their salts, and their hydrates by a process that is (a) cost effective (b) simple (c) easy to operate (d) eco-friendly, (e) consistently give good yields and purity with minimum variables (e) highly reproducible.

The present invention provides such a solution.

OBJECT OF THE INVENTION

The object of the invention is to provide an improved method for the manufacture of single enantiomers of the sulphoxide compounds of the formula (I) and their pharmaceutically acceptable salts and hydrates, thereby resulting in significant economic and technological improvement over the prior art methods.

More specifically, the object of the invention is to manufacture single enantiomers of Omeprazole, Rabeprazole, Lansoprazole or Pantoprazole covered by the formula (I), and pharmaceutically acceptable salts and hydrates.

SUMMARY OF THE INVENTION

Thus, according to one aspect of present invention there is provided a process for preparation of an optically pure or optically enriched enantiomer of a sulphoxide compound of formula (I), said process comprises:

a) providing, a mixture of optical isomers of the sulphoxide compound of formula (I) as starting material, in an organic solvent; the different optical isomers having R and S configurations at the sulfur atom of the sulphoxide group;
b) reacting the mixture of optical isomers, in the organic solvent, with a chiral host;
c) separating the adduct formed by the enantiomer and the chiral host;
d) if desired, repeating the operation of step (b);
e) treating the adduct obtained in step (c) or (d) with a metal base selected from Group I or Group II metal, thereby obtaining the metal salt of the enantiomer of the sulphoxide compound in a substantially optically pure or optically enriched form;
f) optionally, converting the Group I metal salt of substantially optically pure or optically enriched enantiomer of the sulphoxide compound obtained in step (e) to magnesium salt.

DETAILED DESCRIPTION OF THE INVENTION

Figure 1:
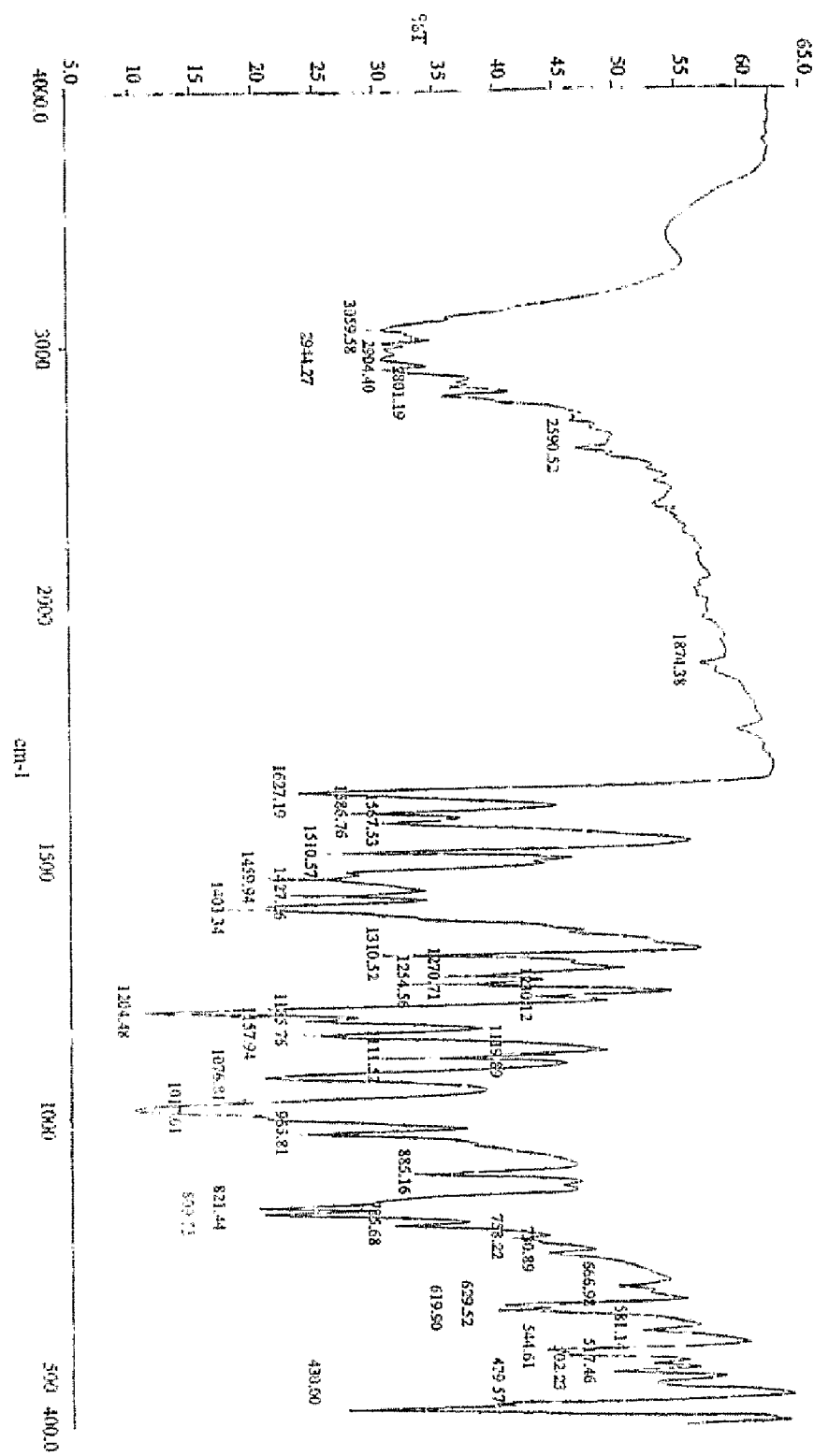
FIG. 1 illustrates an infrared (IR) spectrum of racemic omeprazole.

The invention is directed to a process for preparation of an optically pure or optically enriched enantiomer of a sulphoxide compound of formula (I). Intermediates in the processes of this invention are also part of this invention, as are their salts and hydrates. The sulphoxide compounds suitable as substrates for the process of this aspect of the invention include, for example, omeprazole, lansoprazole, pantoprazole, rabeprazole In a preferred embodiment in step (b), the chiral host is optically pure or optically enriched (S)-(−)-BINOL or (R)-(+)-BINOL.

In a more preferred embodiment, the invention provides a specific process for preparing a substantially optically pure or optically enriched form of omeprazole and its pharmaceutically acceptable salts. In other preferred aspect, the invention also provides an amorphous form of magnesium salt of esomeprazole trihydrate.

The process is depicted in the following Scheme 1

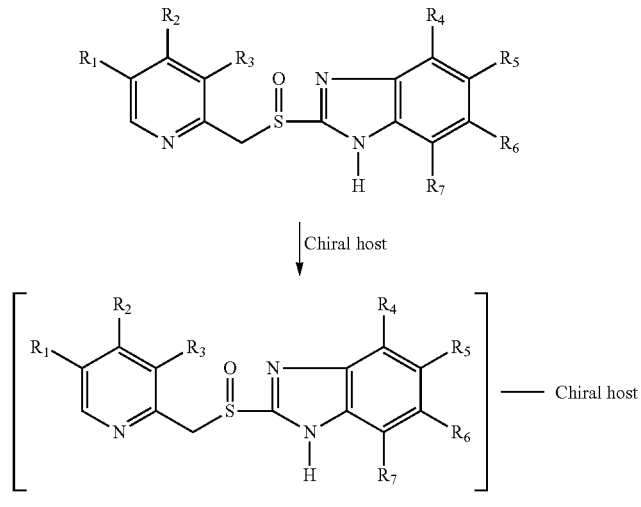

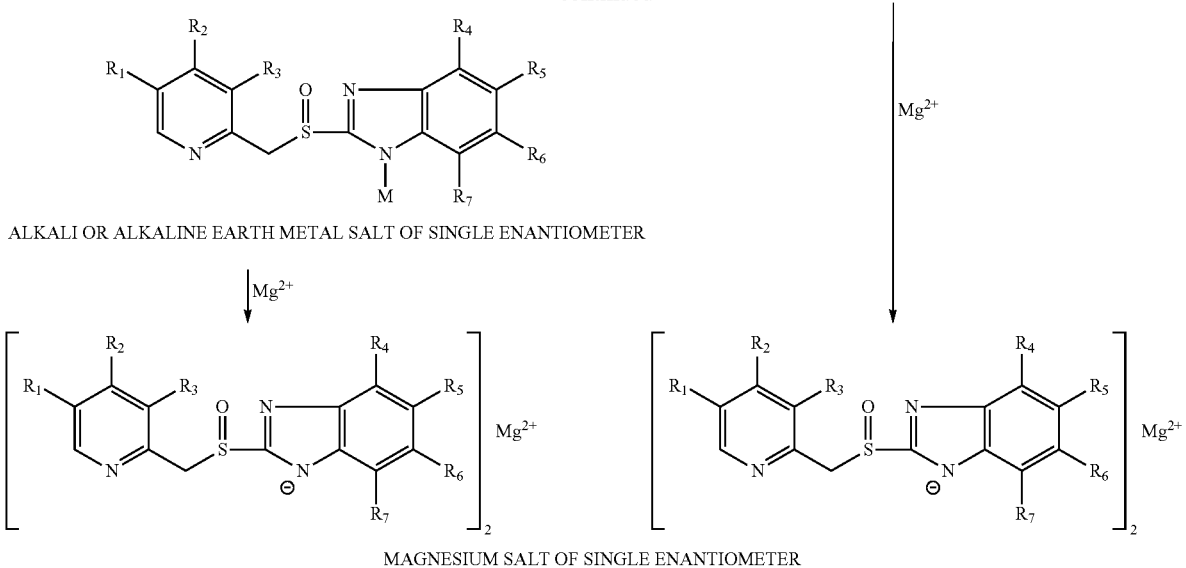

ALKALI OR ALKALINE EARTH METAL SALT OF SINGLE ENANTIOMETER

MAGNESIUM SALT OF SINGLE ENANTIOMETER

In their endeavor to obtain optically pure enantiomer of the sulphoxide compounds of the formula (I), for example the (S)-omeprazole from racemate omeprazole or optically enriched omeprazole by resolution method using BINOL, the present inventors surprisingly found that,
(i) use of mixture of toluene and cyclohexane significantly improved the e.e. value of the inclusion complex of (S)-BINOL and (S)-omeprazole,
(ii) the inclusion complex of (S)-BINOL and (S)-omeprazole can be directly converted to Group I or Group II metal salt of (S)-omeprazole without any further purification of the complex by recrystallization and separation of the host and the guest by chromatography,
(iii) the (S)-BINOL and the other isomer (R)-omeprazole could be recovered and recycled,
(iv) the methodology could be conveniently adopted for other sulphoxide compounds such as Rabeprazole, Lansoprazole, or Pantoprazole, The present method addresses the drawbacks of the resolution using chiral host disclosed in the CN 1223262 by,
(i) providing the chiral complex in very high e.e. in minimum number of operational steps,
(ii) obviates the usage of hexane which is having low flash point,
(iii) utilizes cyclohexane which is a preferred solvent over hexane as the allowed limit of residual solvent for cyclohexane is 3880 ppm, while it is 290 ppm for hexane, in the ICH guideline,
(iv) significantly increases the overall yield through recovering of the chiral material and racemization of the undesired isomer, In one embodiment of the process aspect of the invention, the starting material is a compound of the formula (I). In one variant, $R_1$, $R_2$ are methyl; $R_2$ and $R_5$ are methoxy; and $R_4$, $R_6$, and $R_7$ are hydrogen. In another variant $R_4$, $R_5$, $R_6$, and $R_7$ are hydrogen; $R_1$ is hydrogen; $R_3$ is methyl, and $R_2$ may be —$O(CH_2)_3OCH_3$ or —$OCH_2CF_3$. In a further variant, $R_1$, $R_4$, $R_6$ and $R_7$ are hydrogen; $R_5$ is difluoromethoxy; and $R_2$ and $R_3$ are methoxy. Specific starting materials that are suitable include omeprazole, lansoprazole, rabeprazole, and pantoprazole.

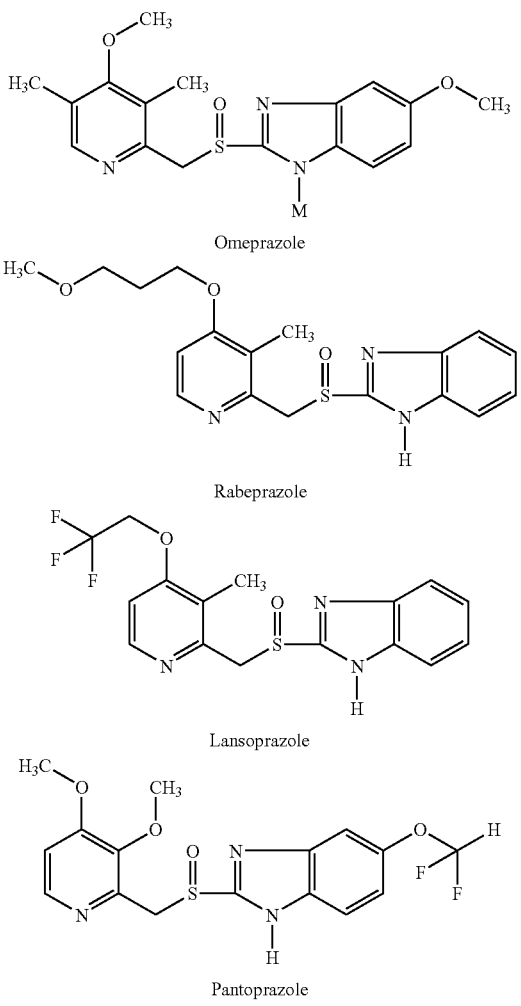

Omeprazole

Rabeprazole

Lansoprazole

Pantoprazole

Initially, a solution of the racemic mixture of the sulphoxide compound of formula (I) is provided in an organic solvent, by suspending or dissolving the compound of formula (I). As used herein, the term "solvent" may be used to refer to a single compound or a mixture of compounds. Suitable organic solvents are preferably alkyl benzenes and cyclohexane. Among the alkyl benzenes, toluene and xylene are preferred. Preferably, the organic solvent is at least a mixture of alkyl benzene such as toluene or xylene and cyclohexane. More preferably, the organic solvent is a mixture of toluene and

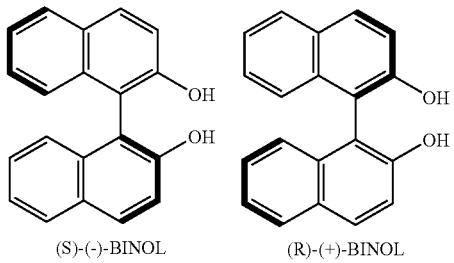

(S)-(-)-BINOL        (R)-(+)-BINOL cyclohexane.

Suitable chiral host include 1,1'-bi-2-naphthol (BINOL), diphenanthrenols or tartaric acid derivatives. Preferably, the (S)-(−)-BINOL or (R)-(+)-BINOL are used. The (S)-(−)-BINOL or (R)-(+)-BINOL may be used in optically pure or optically enriched form.

By mixing the chiral host with the racemate sulphoxide of formula (I) (guest molecules) in the solvent and gently warming to about 50-55° C., the chiral host forms an adduct with one of the enantiomer by a chiral recognition or molecular recognition process. The adduct known as a host-guest inclusion complex is formed via selectively and reversibly including the chiral guest molecules in host lattice through non-covalent interactions such as hydrogen bonding.

The host-guest inclusion complex crystallizes out as solid compound upon lowering the temperature, from ambient to about 0-10° C. The complex was separated out, washed with the solvent. If desired, the separated host-guest inclusion complex may be re-dissolved in the solvent and crystallized out.

By these operations, the process achieves the physical separation of the two enantiomers of the sulphoxide compound of formula (I), one enantiomer in the form of a host-guest inclusion complex and the other enantiomer remains in the solution.

If only one enantiomer is desired, the other may be racemized, in any way known to those skilled in the art, to obtain the starting material sulphoxide of formula (I). The racemization permits increased utilization of the material since the racemized product may be re-used in the process as described.

The adduct is treated with a metal base (MB) where M is the metal of Group I or Group II in an alcoholic solvent selected from methanol, ethanol, isopropanol, and tent-butyl alcohol or mixtures thereof to obtain the corresponding metal salt of optically pure optically enriched enantiomer of the sulphoxide compound of formula (I).

In one embodiment, the adduct is treated with a metal base of Group I metal to obtain an alkali metal salt of optically pure optically enriched enantiomer of the sulphoxide compound of formula (I). The alkali metal salt is then converted to the magnesium salt.

The preferred metal base of Group I metal are potassium hydroxide or sodium hydroxide.

In another embodiment, the adduct is directly converted to the magnesium salt of optically pure optically enriched enantiomer of the sulphoxide compound of formula (I), for instance, by treating with magnesium in methanol.

In a further embodiment, the adduct is first converted to an alkaline earth metal salt such as barium or calcium by treating with their oxide or hydroxide in an alcoholic solvent, and subsequently converted to the magnesium salt.

The preferred embodiment of the process aspect of the invention involves preparation of the (S) enantiomer of omeprazole, known as esomeprazole, and its salts. The scheme 2 illustrates the preferred process contemplated by the inventors.

Racemic omeprazole, was treated with the chiral host (S)-(−)-BINOL, in toluene-cyclohexane (4:1 v/v). A bluish gray adduct, the inclusion complex was formed between the (S)-BINOL and (S)-isomer of omeprazole, which was separated by filtration and washed with a mixture of cyclohexane and toluene. The optical purity of esomeprazole in the complex as measured by HPLC was not less than 99.5% e.e.

Figure 2:
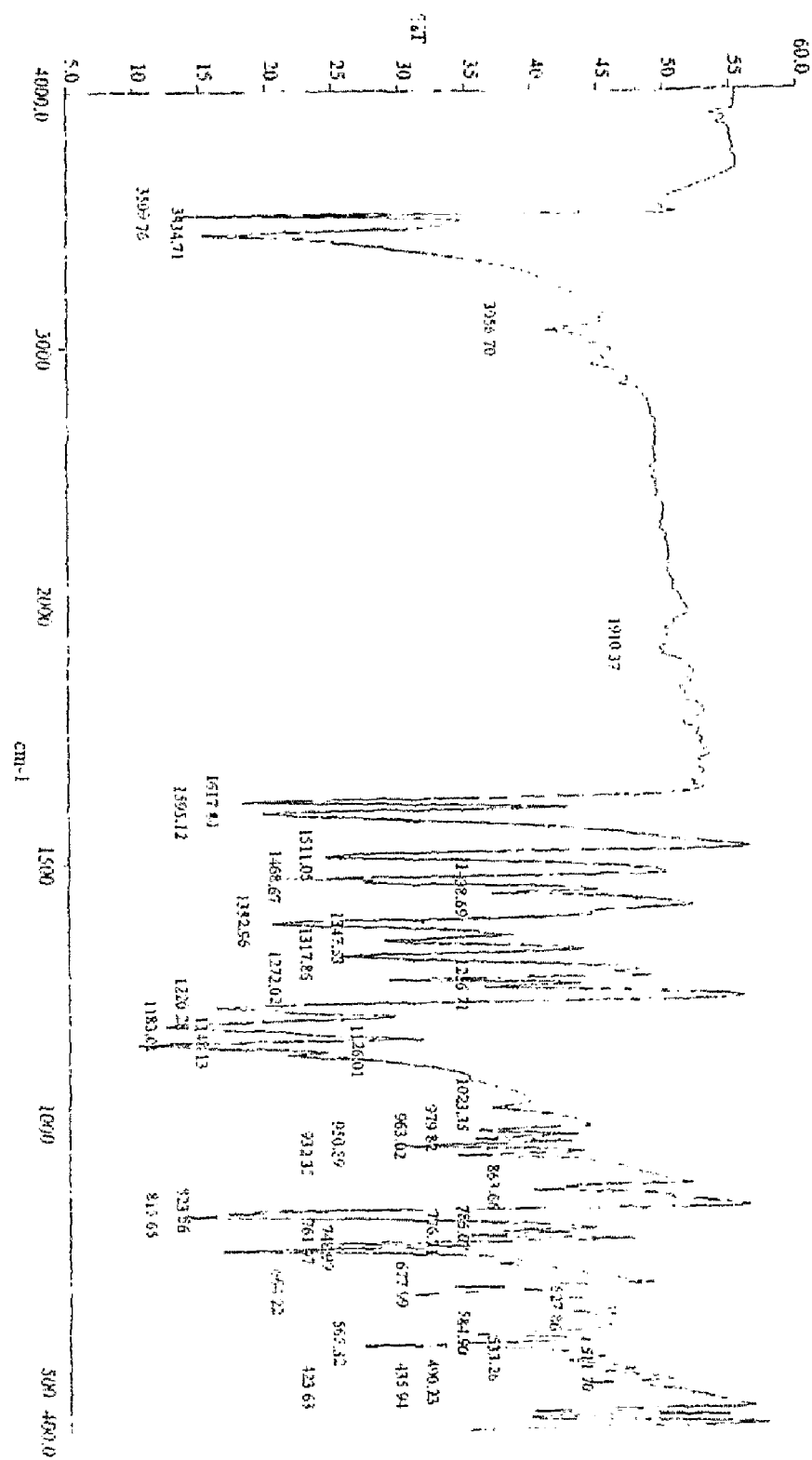
FIG. 2 illustrates an IR spectrum of S-BINOL.
Figure 3:
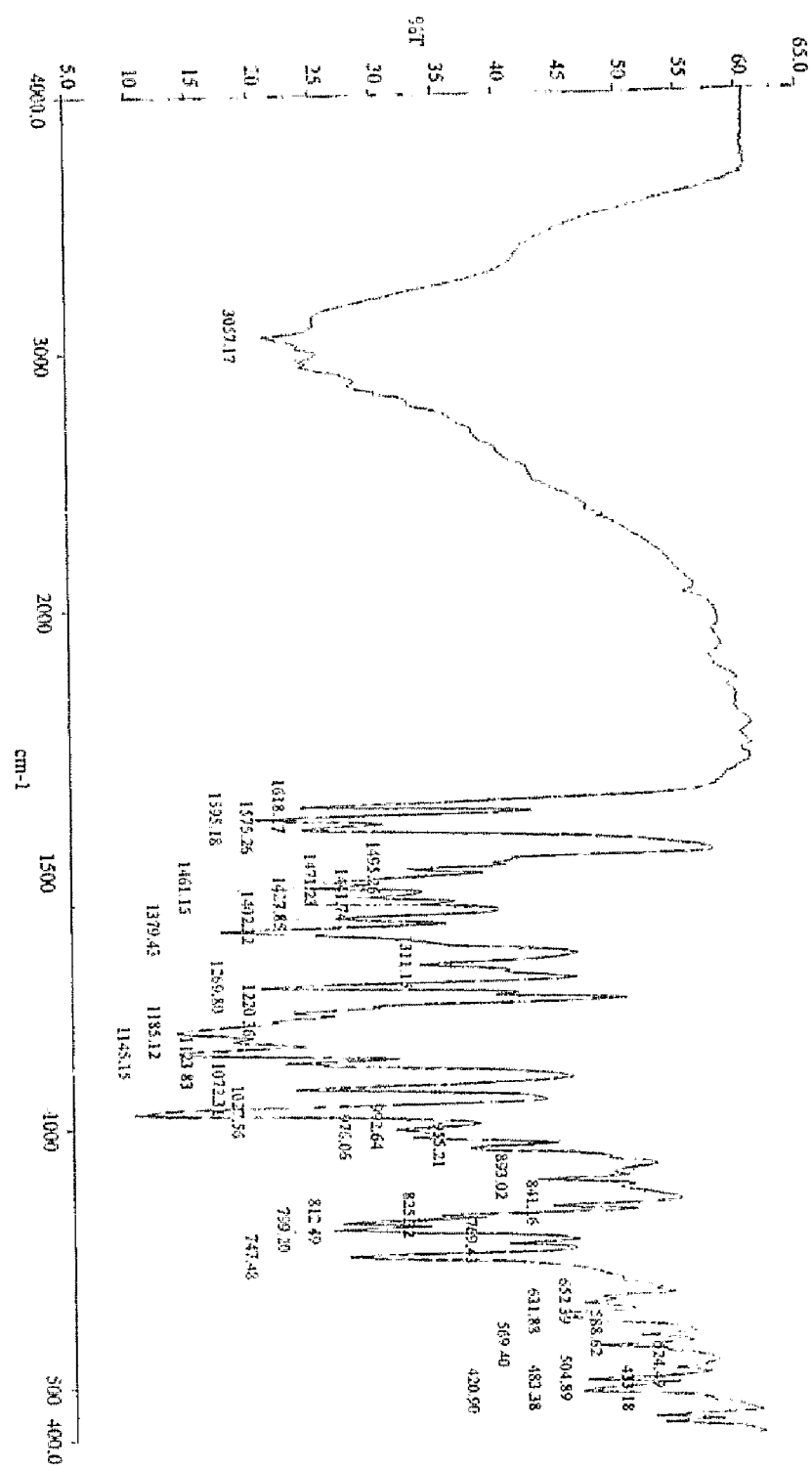
FIG. 3 illustrates an IR spectrum of the host-guest inclusion complex including S-BINOL and esomeprazole.

The IR-spectra of racemic omeprazole, (S)-BINOL and the host-guest inclusion complex is provided in FIGS. 1, 2, and 3 respectively. There is no significant difference in the stretching frequency of S=O bond in racemate omeprazole (1017 cm$^{-1}$) as compared to the stretching frequency of 1028 cm$^{-1}$ in the inclusion complex.

The adduct isolated is treated with potassium hydroxide or sodium hydroxide in an alcoholic solvent selected from methanol, ethanol, isopropanol, and tent-butyl alcohol or mixtures thereof to obtain the potassium or sodium metal salt of optically pure optically enriched enantiomer of the sulphoxide compound of formula (I).

The sodium or potassium salt of optically pure optically enriched enantiomer of the sulphoxide compound of formula (I) is converted to magnesium salt by treating with $MgSO_4$.

In another embodiment the (S)-omeprazole-(S)-(−)-BINOL adduct is converted directly to its magnesium salt by treating with magnesium in methanol as depicted in Scheme 2.

Figure 5:
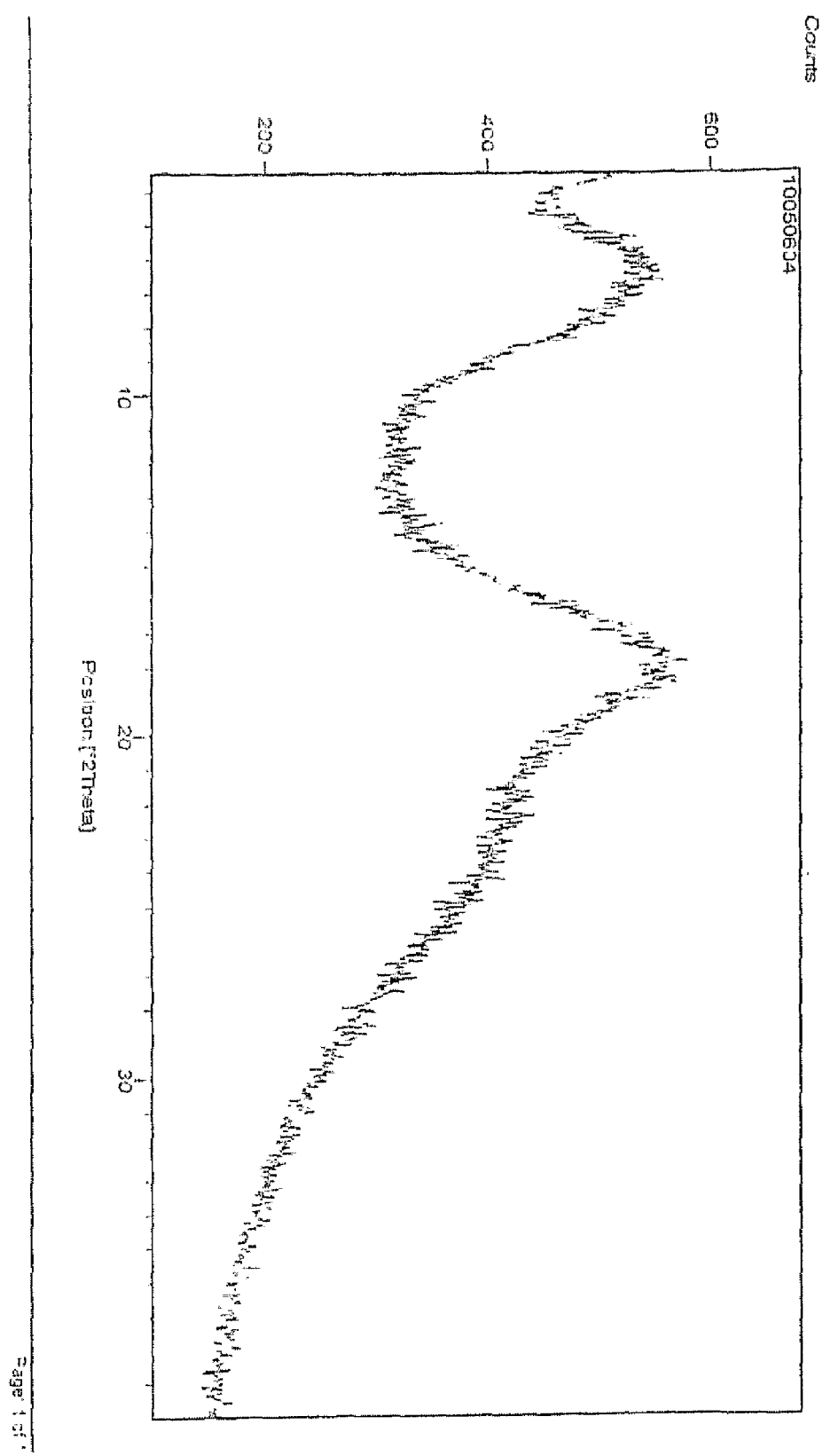
FIG. 5 illustrates an X-ray powder diffraction pattern of an amorphous form of esomeprazole magnesium salt.

The esomeprazole magnesium obtained by the process is in an amorphous form characterized by powder X-ray diffraction pattern given in FIG. 5.

Scheme 2

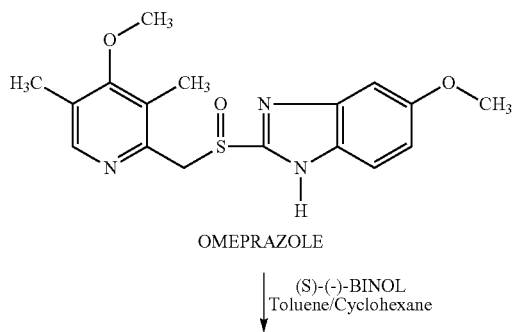

OMEPRAZOLE (S)-(−)-BINOL
Toluene/Cyclohexane

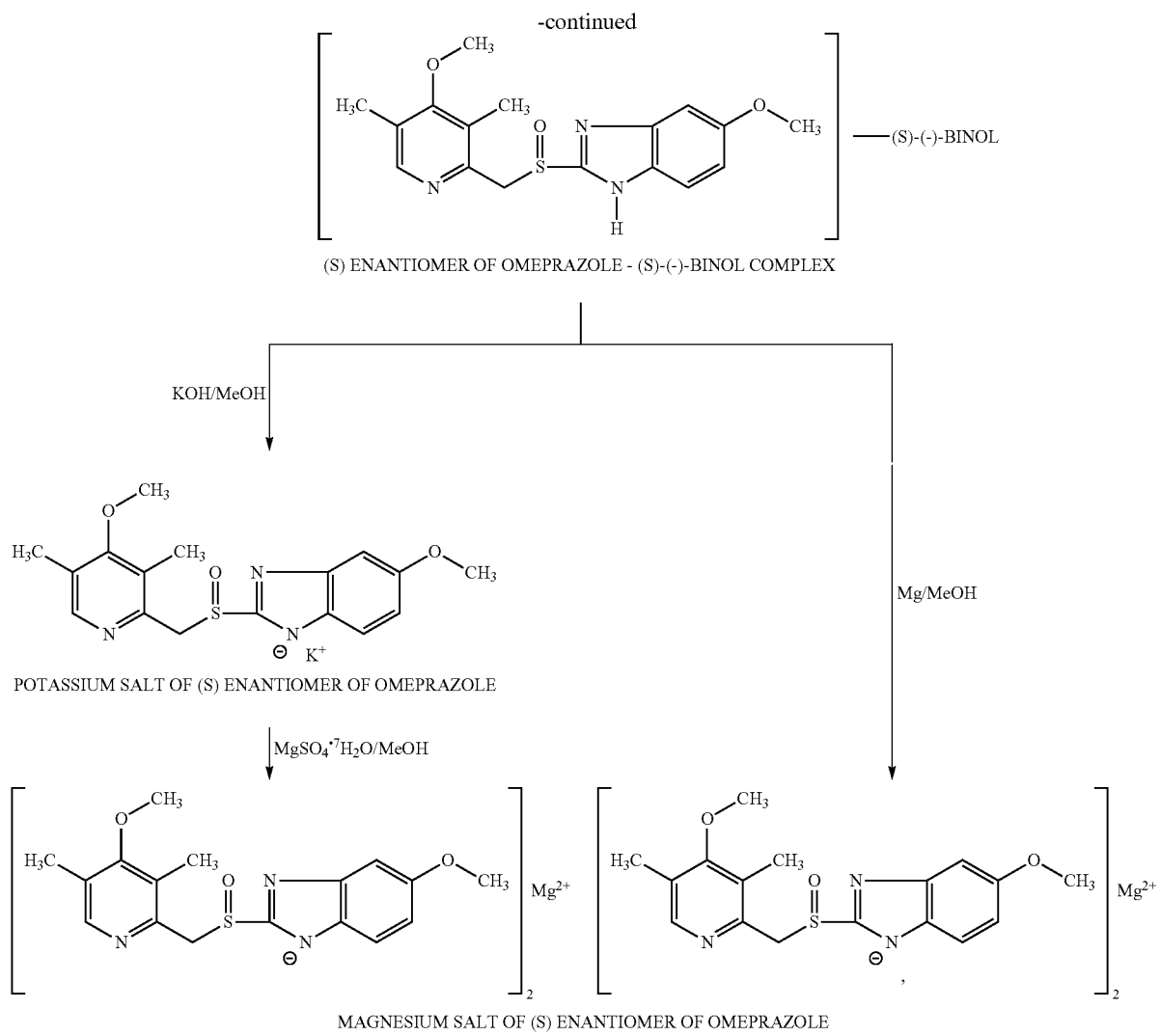

Alternatively, if (R)-enantiomer of omeprazoele is desired, (R)-(+)-BINOL may be used in the process described above.

The following examples illustrate the practice of the invention without being limiting any way.

EXAMPLE 1

Preparation of (S)-omeprazole-(S)-(−)-BINOL complex

Omeprazole (100 g, 0.2898 mole) was added to a mixture of toluene (1600 ml) and cyclohexane (400 ml) in a round bottom flask kept at 25-30° C. (S)-(−)-BINOL (124.3 g, 0.4346 mole) was added and the content warmed to about 50-55° C. with stirring for 30-45 minutes. The content of the flask was allowed to attain the ambient temperature and then cooled to 0-5° C. with stirring for about an hour. The (S)-omeprazole-(S)-(−)-BINOL complex crystallizes out, filtered and washed with a mixture of cyclohexane/toluene (1:4, v/v) pre-cooled to 0-5° C. The (S)-omeprazole-(S)-(−)-BINOL complex was dried at 35-40° C. under reduced pressure. The e.e. of (S)-omeprazole in the complex was found to be 99.5%. Yield: 85%.

Figure 4:
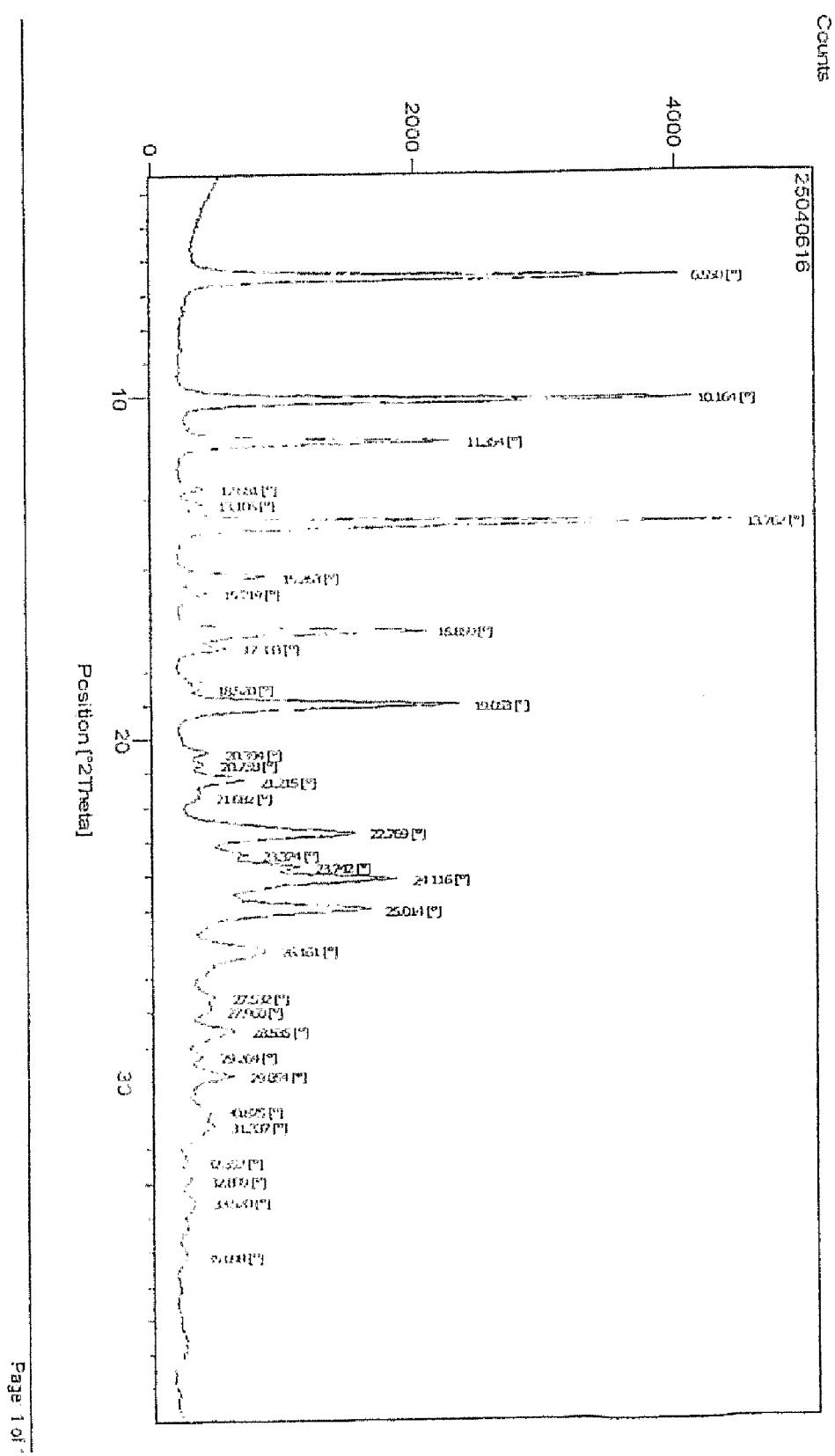
FIG. 4 illustrates an X-ray powder diffraction pattern of the host-guest inclusion complex including S-BINOL and esomeprazole.

The IR spectrum of the complex is given in FIG. 3. The powder X-ray diffraction pattern is given in FIG. 4

EXAMPLE 2

Preparation of Esompeprazole Potassium Salt

To a solution of potassium hydroxide (31 g, 0.5535 mole) in methanol (500 ml) kept in a round bottom flask was added (S)-omeprazole-(S)-(−)-BINOL complex (100 g, 0.1584 mole) with stirring at 25-30° C. The content of the flask were stirred for about 2-2.5 hrs at 25-30° C. and then cooled to 0-5° C. and stirred for a further period of about 1-1.5 hrs. The potassium salt of esomeprazole was filtered, washed with cold methanol (50 ml), followed by washing with cold acetone (100 ml) and dried under suction. The optical purity of esompeprazole potassium as tested by HPLC was not less than 99.5%. Yield: 80%.

EXAMPLE 3

Preparation of Esomeprazole Magnesium Salt

To a solution of esomeprazole potassium salt (100 g, 0.261 mole) in methanol (500 ml) kept in a round bottom flask, was added magnesium sulphate heptahydrate (64.1 g, 0.26 mole) at 25-30° C. and stirred for 1.5-2 hrs. The insoluble material formed was filtered off and the filtrate was passed through a 0.45 micron membrane filter. To the filtrate, water (1300 ml) was added and stirred at 25-30° C. for 1-1.5 hrs, cooled to 0-5° C., and stirred for a further period of 1-1.5 hrs. The solid formed was collected by filtration and washed with water and dried under reduced pressure at 40-45° C. to obtain the esomeprazole magnesium salt.
Yield: 45%.
Optical purity: 100%
Optical rotation: $[\alpha]_D = -142.04°$ at 25° C. and c=0.5% in methanol
e.e.: 100%

The esomeprazole magnesium salt obtained is in an amorphous form as characterized by its powder X-ray diffraction pattern given in FIG. 5.

The moisture content of the product is 7.5% by TGA, indicating that the product is a trihydrate.

EXAMPLE 4

Preparation of Esomeprazole Magnesium Salt

To a suspension of Magnesium turnings (0.5 g, 0.0208 mole) in methanol (15 ml) was added methylene chloride (0.5 ml), stirred for about 1.5-2 hrs at 55-60° C. (S)-omeprazole-(S)-(–)-BINOL complex (2 g, 0.0030 moles) was added and stirred for 45-60 minutes. The insoluble salts were filtered off. To the combined filtrate was added water (30 ml), stirred for about 45-60 minutes and cooled to 0-5° C. to obtain a solid, which was collected by filtration and dried.
Yield: 35.4%
e.e.: 99.6%
optical purity: 99.8%

EXAMPLE 5

Preparation of (S)-rabeprazole-(S)-(–)-BINOL complex

To a mixture of toluene (100 ml) and cyclohexane (150 ml) in a round bottom flask was added rabeprazole (10 g, 0.0278 mole), and gently warmed to 48-52° C. for 30-45 minutes. The reaction mass was cooled to 25-30° C. and further cooled to 3-8° C., stirred for 45-60 minutes to isolate a solid product, which was washed with cold cyclohexane-toluene (1:1 v/v). The product was dried at 35-40° C. under reduced pressure.
Yield: 55.6%
e.e.: 99.8%
optical purity: 99.9%

The invention claimed is:

1. A process for preparation of an optically pure or optically enriched enantiomer of a sulphoxide compound of formula (I), said process consisting essentially of:
   a) providing a mixture of enantiomers of the sulphoxide compound of formula (I) as starting material, in an organic solvent; said enantiomers having R and S configurations at the sulfur atom of the sulphoxide group;
   b) treating the mixture of enantiomers, in the organic solvent, with (S)-(–)-BINOL;
   c) separating the adduct formed by the enantiomer and (S)-(–)-BINOL;
   d) if desired, repeating the operation of step (b);
   e) treating the adduct obtained in step (c) or (d) with metal base selected from Group I and Group II metal, thereby obtaining metal salt of one of the optical isomers of the sulphoxide compound in optically pure or optically enriched form;
   f) optionally, reacting the Group I metal salt of optically pure or optically enriched form the optical isomers of the sulphoxide compound obtained in step (e) to magnesium salt

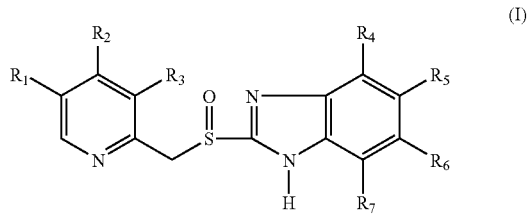

wherein the substituents in Formula (I) can be same or different selected from the following where $R_1$ is H or -Me; $R_2$ is H or —OMe; $R_3$ is H, -Me, or —OMe; $R_4$ is H or —OMe; $R_5$ is H, —OMe, or difluoromethoxy; $R_6$ is H, —O(CH$_2$)$_3$OCH$_3$, or —OCH2CF$_3$; and $R_7$ is H or CH$_3$.

2. A process according to claim 1, wherein the optical purity of the enantiomer of the sulphoxide compound of formula (I) is at least 99.5%.

3. The process according to claim 1, wherein $R_1$ and $R_3$ are methyl; $R_2$ and $R_5$ are methoxy; and $R_4$, $R_6$, and $R_7$ are hydrogen.

4. The process according to claim 1, wherein $R_1$, $R_4$, $R_6$, and $R_7$ are hydrogen; $R_5$ is difluoromethoxy; and $R_3$ and $R_4$ are methoxy.

5. The process according to claim 1, wherein $R_1$, $R_2$, $R_3$, and $R_4$ are hydrogen.

6. The process according to claim 5, wherein $R_5$ is hydrogen and $R_7$ is methyl.

7. The process according to claim 6, wherein $R_6$ is —O(CH$_2$)$_3$OCH$_3$.

8. The process according to claim 6, wherein $R_6$ is —OCH$_2$CF$_3$.

9. The process according to claim 1, wherein the organic solvent is a mixture of alkyl benzene and cyclohexane.

10. The process according to claim 9, wherein the organic solvent is a mixture of toluene and cyclohexane.

11. The process according to claim 1, wherein the reaction of the adduct to the Group I or Group II metal salt of the enantiomer by treating with a oxide or hydroxide of Group I or Group II metal is carried out in an alcoholic solvent selected from methanol, ethanol, isopropanol, and isobutyl alcohol.

12. The process according to claim 11 wherein the Group I metal is selected from lithium, sodium, and potassium.

13. The process according to claim 11, wherein the Group II metal is selected from magnesium, calcium and barium.

14. The process according to claim 1, wherein said starting material is omeprazole.

15. The process according to claim 14, wherein the said adduct is a host-guest complex of (S) enantiomer of omeprazole with (S)-(–)-BINOL.

16. The process according to claim 14, wherein the host-guest complex of (S) enantiomer of omeprazole with (S)-(–)-BINOL is treated with potassium hydroxide in methanol.

17. The process according to claim 15, wherein the host-guest complex of (S) enantiomer of omeprazole with (S)-(–)-BINOL is treated with magnesium in methanol.

18. The process according to claim 14, wherein the said product is potassium salt of (S) enantiomer of omeprazole.

19. The process according to claim 14, wherein the product is magnesium salt of esomeprazole.

20. The process according to claim 11, wherein said solvent is methanol.

21. The process of claim 1, wherein the mixture in b) consists of the mixture of enantiomers, the organic solvent, and the (S)-(−)-BINOL.

22. The process of claim 21, wherein the mixture in a) consists of the mixture of enantiomers and the organic solvent.

23. The process of claim 20, wherein the solvent consists of alkyl benzene and cyclohexane.

24. A process for preparing an optically pure or optically enriched enantiomer of a sulphoxide compound of formula (I)

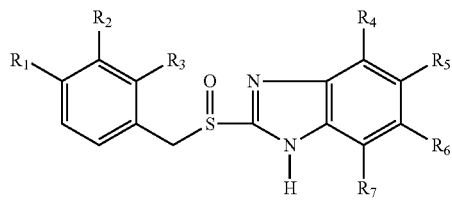

where $R_1$ is H or -Me; $R_2$ is H or —OMe; $R_3$ is H, -Me, or —OMe; $R_4$ is H or —OMe; $R_5$ is H, —OMe, or difluoromethoxy; $R_6$ is H, —O(CH$_2$)$_3$OCH$_3$, or —OCH2CF$_3$; $R_7$ is H or CH$_3$; and the substituents can be the same or different;

the process comprising:

providing a mixture consisting of enantiomers of the sulphoxide compound of formula (I) and an organic solvent, the enantiomers having R and S configurations at the sulfur atom of the sulphoxide group;

adding (S)-(−)-BINOL to the mixture consisting of enantiomers of the sulphoxide compound of formula (I) and an organic solvent to form a mixture consisting of mixture consisting of enantiomers of the sulphoxide compound of formula (I), the organic solvent, the (S)-(−)-BINOL, and an adduct of the enantiomer and (S)-(−)-BINOL;

separating the adduct formed by the enantiomer and (S)-(−)-BINOL;

optionally, repeating the adding of (S)-(−)-BINOL and obtaining the adduct;

treating the adduct obtained with metal base selected from Group I and Group II metal and obtaining a metal salt of one of the optical isomers of the sulphoxide compound in optically pure or optically enriched form;

optionally, reacting the Group I metal salt of optically pure or optically enriched form the optical isomers of the sulphoxide compound obtained in step (e) to magnesium salt.

* * * * *